(12) United States Patent
Min

(10) Patent No.: US 7,574,255 B1
(45) Date of Patent: *Aug. 11, 2009

(54) CRITERIA FOR MONITORING INTRATHORACIC IMPEDANCE

(75) Inventor: Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 507 days.

This patent is subject to a terminal disclaimer.

(21) Appl. No.: 11/269,234

(22) Filed: Nov. 7, 2005

(51) Int. Cl.
*A61B 5/00* (2006.01)
*A61B 5/02* (2006.01)
*A61B 5/05* (2006.01)
*A61B 5/08* (2006.01)

(52) U.S. Cl. .................. 600/547; 600/300; 600/481; 600/484; 600/529

(58) Field of Classification Search .............. 600/300, 600/481, 484, 529, 547
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 5,466,254 A | 11/1995 | Helland | 607/123 |
| 5,476,483 A | 12/1995 | Bornzin et al. | 607/17 |
| 6,045,513 A * | 4/2000 | Stone et al. | 600/508 |
| 6,314,323 B1 | 11/2001 | Ekwall | 607/23 |
| 6,409,675 B1 | 6/2002 | Turcott | |
| 6,473,640 B1 | 10/2002 | Erlebacher | 600/547 |
| 6,512,949 B1 | 1/2003 | Combs et al. | 600/547 |
| 6,645,153 B2 * | 11/2003 | Kroll et al. | 600/481 |
| 7,155,281 B1 * | 12/2006 | Fayram | 607/19 |
| 7,171,271 B2 * | 1/2007 | Koh et al. | 607/19 |
| 2002/0183584 A1 * | 12/2002 | Shannon et al. | 600/16 |
| 2003/0028221 A1 * | 2/2003 | Zhu et al. | 607/9 |
| 2003/0055345 A1 | 3/2003 | Eigler et al. | 600/486 |
| 2004/0167580 A1 | 8/2004 | Mann et al. | |
| 2004/0172080 A1 | 9/2004 | Stadler et al. | |
| 2006/0235325 A1 | 10/2006 | Holmstrom et al. | |

FOREIGN PATENT DOCUMENTS

EP    1 011 802 B1    8/1998

OTHER PUBLICATIONS

Final Office Action, mailed Dec. 14, 2007: Related U.S. Appl. No. 11/269,391.
Non-Final Office Action, mailed Mar. 18, 2008: Related U.S. Appl. No. 11/269,391.
First Office Action, mailed Jun. 27, 2007: Related U.S. Appl. No. 11/269,391.
Agricola, Eustachio MD et al., "*Ultrasound Comet-Tail Images*": A marker of Pulmonary Edema, CHEST 2005; 127:1690-1695.

(Continued)

*Primary Examiner*—Patricia C Mallari

(57) ABSTRACT

An exemplary method includes providing information (e.g., a left atrial pressure, a NYHA class, echocardiographic information, etc.), based at least in part on the information, determining a weight and, based at least in part on the weight, determining a threshold for use in intrathoracic impedance monitoring. Such an exemplary method may include comparing an intrathoracic impedance to the threshold, comparing an intrathoracic impedance change to the threshold, or comparing a product of intrathoracic impedance and time to the threshold. Various exemplary methods, devices, systems, etc., are disclosed.

4 Claims, 11 Drawing Sheets

OTHER PUBLICATIONS

Cowie, Martin R. MD, "Monitoring Heart Failure using an Implantable Device Measuring Intrathoracic Impedance—Technical and Clinical Overview," Business Briefing: *European Cardiology* 2005, pp. 62-65.

Drake, R.E. and Doursout, M.F., "*Pulmonary Edema and Elevated Left Atrial Pressure: Four Hours and Beyond*," News Physiol Sci 17: 223-226, 2002.

Erdman, A. John, III et al., "*Effect of Increased Vascular Pressure on Lung Fluid Balance in Unanesthetized Sheep*," Circ Res. Sep. 1975;37(3): 271-84.

Hofmann, Thomas MD et al., "*Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function*," J Am Coll Cardiol 1995;26:23-49.

Shioi, Tetsuo MD, et al., "*Rapamycin Attenuates Lead-Induced Cardiac Hypertrophy in Mice*," Circulation, 2003; 107:1664-1670.

Tsukada, Kosuke et al., "*Development of Catheter-Type Optical Oxygen Sensor and Applications to Bioinstrumentation*," Biosensors and Bioelectronics 18 (2003) 1439-1445.

Final Office Action, mailed Aug. 28, 2008: Related U.S. Appl. No. 11/269,391.

NonFinal Office Action, mailed Nov. 18, 2008: Related U.S. Appl. No. 11/269,390.

* cited by examiner

Exemplary Table 720

| LA Pressure | NYHA Class | Weight ($W_Y$) | Threshold % |
|---|---|---|---|
| P < X1 | I | $W_Y = 1.2$ | 1.2*Y |
| X1 < P < X2 | II | $W_Y = 1$ | Y |
| X2 < P < X3 | III | $W_Y = 0.8$ | 0.8*Y |
| P > X3 | IV | $W_Y = 0.6$ | 0.6*Y |

Exemplary Table 730

| LA Pressure | NYHA Class | Weight ($W_I$) | Ohm-Days |
|---|---|---|---|
| P < X1 | I | $W_I = 1.3$ | $1.3*I_{OD}$ |
| X1 < P < X2 | II | $W_I = 1$ | $I_{OD}$ |
| X2 < P < X3 | III | $W_I = 0.75$ | $0.75*I_{OD}$ |
| P > X3 | IV | $W_I = 0.65$ | $0.65*I_{OD}$ |

CRITERIA FOR MONITORING INTRATHORACIC IMPEDANCE

CROSS REFERENCE TO RELATED APPLICATIONS

This application is related to U.S. patent applications: 1) Ser. No. 11/269,390, filed Nov. 7, 2005, titled "Criteria for Monitoring Intrathoracic Impedance"; and 2) Ser. No. 11/269,234, filed Nov. 7, 2005, titled "Criteria for Monitoring Intrathoracic Impedance".

TECHNICAL FIELD

Subject matter presented herein generally relates to determining an appropriate criterion or criteria for monitoring intrathoracic impedance using an implantable device.

BACKGROUND

Heart failure patients are at a heightened risk of developing pulmonary edema. For example, as left-side cardiac function deteriorates, left atrial pressure can increase and cause lung capillary hypertension. Hypertension can cause fluid to accumulate first in interstitial lung space and then in alveolar or lung airspace. In a worst case scenario, excessive or prolonged hypertension causes rupture of lung capillaries. Consequently, a need exists for techniques to monitor onset and degree of pulmonary edema. Various exemplary technologies presented herein aim to address this need and other needs.

SUMMARY

An exemplary method includes providing information (e.g., a left atrial pressure, a NYHA class, echocardiographic information, etc.), based at least in part on the information, determining a weight and, based at least in part on the weight, determining a threshold for use in intrathoracic impedance monitoring. Such an exemplary method may include comparing an intrathoracic impedance to the threshold, comparing an intrathoracic impedance change to the threshold, or comparing a product of intrathoracic impedance and time to the threshold. Various exemplary methods, devices, systems, etc., are disclosed.

In general, the various methods, devices, systems, etc., described herein, and equivalents thereof, are optionally suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Various exemplary methods, devices, systems, etc., described herein pertain to monitoring intrathoracic impedance using an implantable device. Various exemplary techniques are disclosed herein to determine one or more criteria to trigger an alarm or call for other action when a change or changes occur in intrathoracic impedance. Such techniques optionally account for various phases or underlying mechanisms associated with pulmonary edema. Various exemplary techniques use echocardiograph information to determine one or more criteria. A particular technique analyzes echocardiograph comet-tails to provide a score indicative of the presence of or the degree of pulmonary edema and, in turn, a weight for use in determining a threshold for use in monitoring intrathoracic impedance.

Exemplary Stimulation Device

The techniques described below are optionally implemented in connection with any stimulation device that is configured or configurable to stimulate and/or shock tissue.

Figure 1:
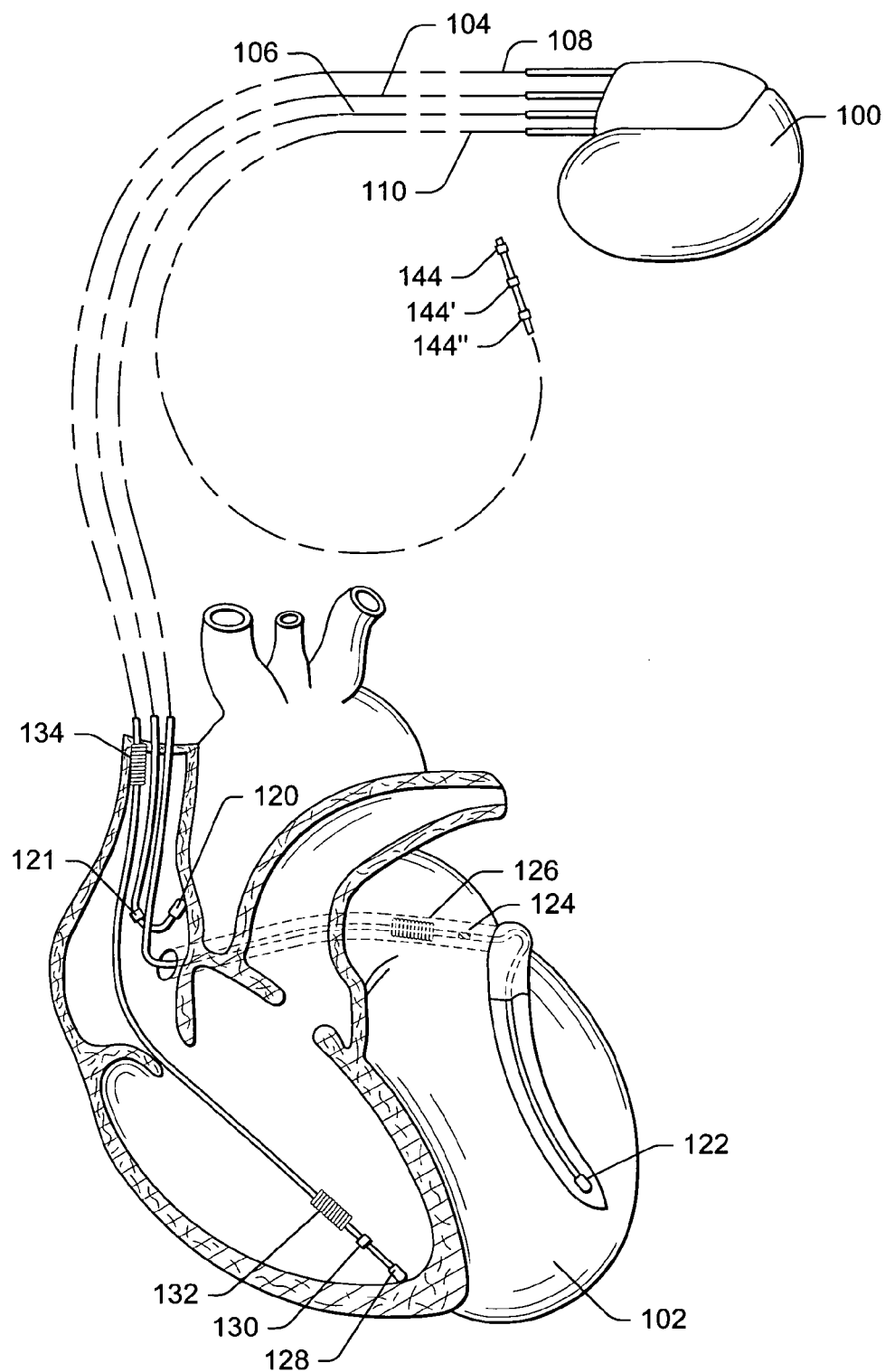
FIG. 1 is a simplified diagram illustrating an exemplary implantable device in electrical communication with various leads. A suitable implantable device may include fewer or more leads.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for stimulation of autonomic nerves, non-myocardial tissue, other nerves, etc. For example, this lead may be positioned in and/or near a patient's heart or near an autonomic nerve within a patient's body and remote from the heart. As another example, such a lead may be positioned within a patient's body for purposes of impedance measurements. While four leads 104, 106, 108, 110 are shown in FIG. 1, a device may have fewer or more leads.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
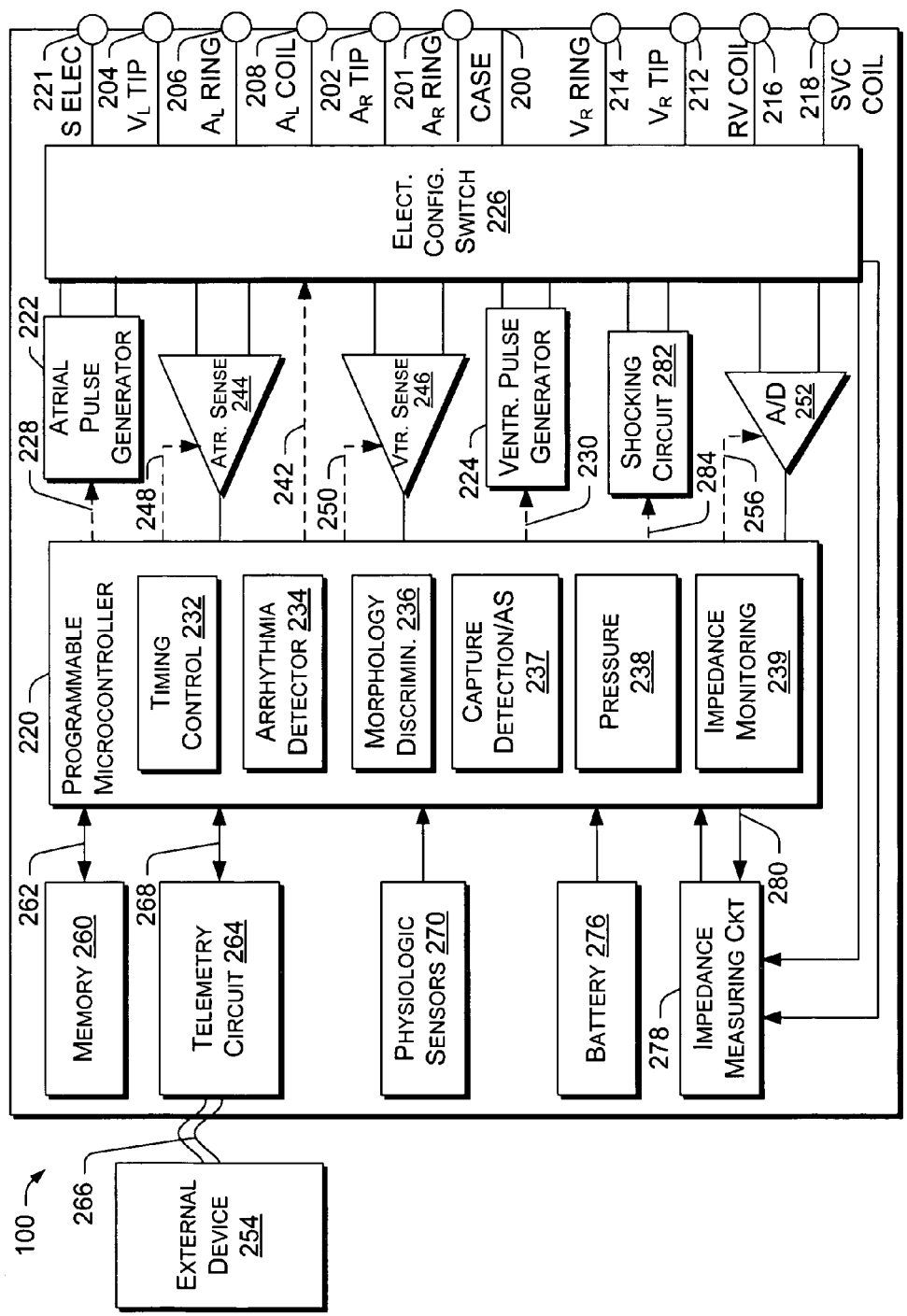
FIG. 2 is a functional block diagram of an exemplary implantable device illustrating basic elements that are configured to provide, for example, sensing, cardioversion, defibrillation, pacing stimulation or other tissue or nerve stimulation.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, various techniques described herein can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc. Further, various techniques described herein can be implemented in conjunction with an implantable device suited for monitoring intrathoracic impedance where such a device may or may not have stimulation capabilities.

Housing 200 for the implantable device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy and sensing. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrioventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology discrimination module 236, a capture detection/sensitivity module 237, a pressure analysis module 238, an impedance monitoring module 239 and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The pressure analysis module 238 may perform a variety of tasks related to one or more measures of pressure and is optionally utilized by the stimulation device 100 in determining a patient's hemodynamic profile. The impedance monitoring module 239 may perform a variety of tasks related to impedance monitoring, as discussed in more detail below.

The pressure analysis module 238 and the impedance monitoring module 239 may be implemented in hardware as part of the microcontroller 220, or as software/firmware instructions programmed into the device and executed on the microcontroller 220 during certain modes of operation. The impedance monitoring module 239 may optionally implement various exemplary methods described herein. The impedance monitoring module 239 may be responsible for implementing intrathoracic impedance monitoring and determining, selecting or adjusting settings related thereto.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

Pressure sensors for sensing left atrial pressure are discussed in U.S. Patent Application US2003/0055345 A1, to Eigler et al., which is incorporated by reference herein. The discussion pertains to a pressure transducer permanently implantable within the left atrium of the patient's heart and operable to generate electrical signals indicative of fluid pressures within the patient's left atrium. According to Eigler et al., the pressure transducer is connected to a flexible electrical lead, which is connected in turn to electrical circuitry, which includes digital circuitry for processing electrical signals. Noted positions of the transducer include within the left atrium, within a pulmonary vein, within the left atrial appendage and in the septal wall. Control of or acquisition of information from a pressure sensor is optionally by the pressure module 238. Such information is optionally used by the impedance monitoring module 239, for example, to determine one or more criteria related to monitoring intrathoracic impedance.

The exemplary device 100 optionally includes a connector capable of connecting a lead that includes a pressure sensor. For example, the connector 221 optionally connects to a pressure sensor capable of receiving information pertaining to chamber pressures or other pressures. Pressure information is optionally processed or analyzed by the pressure analysis module 238 and optionally used by the impedance monitoring module 239.

A study by Hofmann et al., "Simultaneous measurement of pulmonary venous flow by intravascular catheter Doppler velocimetry and transesophageal Doppler echocardiography: relation to left atrial pressure and left atrial and left ventricular function", *J Am Coll Cardiol.* 1995 July; 26(1):239-49, used a "microtip" pressure transducer and noted that mean left atrial pressure was strongly correlated with the ratio of systolic to diastolic peak velocity, systolic velocity-time integral, time to maximal flow velocity and the ratio of systolic to diastolic flow duration.

Commercially available pressure transducers include those marketed by Millar Instruments (Houston, Tex.) under the mark MIKROTIP®. A study by Shioi et al., "Rapamycin Attenuates Load-Induced Cardiac Hypertrophy in Mice", *Circulation* 2003; 107:1664, measured left ventricular pressures in mice using a Millar pressure transducer inserted through the LV apex and secured in the LV apex with a purse-string suture using 5-0 silk. Various exemplary methods, devices, systems, etc., described herein optionally use such a pressure transducer to measure pressures in the body (e.g., chamber of heart, vessel, etc.).

In various exemplary methods, while direct measurement of pulmonary artery diastolic pressure would be helpful, one or more surrogate or alternative measurements (e.g., LA pressure, right ventricular outflow tract pressure, etc.) may be used and, where appropriate or desirable, such measures may be used to estimate pulmonary artery diastolic pressure.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense pressure, respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

Other sensors may be used, including, but not limited to, oxygen sensors. Technology exists for lead-based oximeters. For example, a study by Tsukada et al., "Development of catheter-type optical oxygen sensor and applications to bio-instrumentation," *Biosens Bioelectron,* 2003 Oct. 15; 18(12): 1439-45, reported use of a catheter-type optical oxygen sensor based on phosphorescence lifetime.

The exemplary device 100 optionally includes a connector capable of connecting a lead that includes a sensor for sensing pressure, oxygen information, etc. For example, the connector 221 optionally connects to a sensor for sensing information related to pressure or blood oxygen concentration. Such information is optionally processed or analyzed by the pressure analysis module 238, the impedance monitoring module 239, or other module.

The physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device 100 optionally includes circuitry capable of sensing heart sounds and/or vibration associated with events that produce heart sounds. Such circuitry may include an accelerometer as conventionally used for patient position and/or activity determinations. Accelerometers typically include two or three sensors aligned along orthogonal axes. For example, a commercially available micro-electromechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 mm$^3$). The ADXL202 MEMS is a dual-axis accelerometer on a single monolithic integrated circuit and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL202 MEMS includes micro-circuitry and a mechanical oscillator.

While an accelerometer may be included in the case of an implantable pulse generator device, alternatively, an accelerometer communicates with such a device via a lead or through electrical signals conducted by body tissue and/or fluid. In the latter instance, the accelerometer may be positioned to advantageously sense vibrations associated with cardiac events. For example, an epicardial accelerometer may have improved signal to noise for cardiac events compared to an accelerometer housed in a case of an implanted pulse generator device.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264. Trigger IEGM storage also can be achieved by magnet.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds (HF indications—pulmonary edema and other factors); detecting when the device has been implanted; measuring stroke volume; and detecting the opening of heart valves, etc. The impedance measuring circuit 278 is advantageously coupled to the switch 226 so that any desired electrode may be used.

The impedance measuring circuit 278 may provide for acquisition of intrathoracic impedance measurements. For example, an impedance measurement between a cardiac electrode (e.g., of one of the leads 104, 106, 108) and a case electrode of the device 100 may be acquired and used by the impedance monitoring module 239. Of course, other electrode configurations are possible. Impedance measurements may rely on bipolar or other multi-polar configurations. As described herein, intrathoracic impedance includes intracardiac impedance. Intracardiac impedance pertains to impedance primarily in or across the heart, for example, measured using two or more electrodes positioned in the heart or a vessel of the heart (e.g., epicardial vein, etc.).

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the ICD device initiates defibrillation therapy.

While an ICD device may reserve defibrillation as a latter tier therapy, it may use defibrillation as a first-tier therapy for VF. In general, an ICD device does not synchronize defibrillation therapy with any given portion of a ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Figure 3:
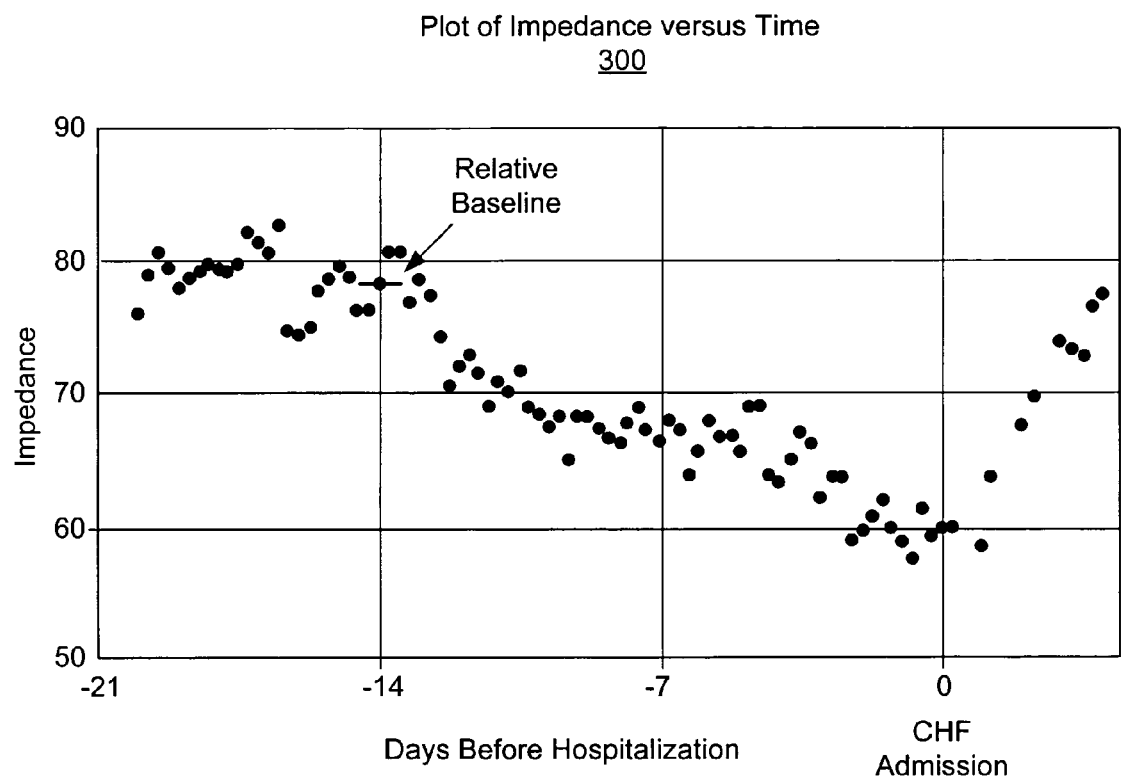
FIG. 3 is a plot of intrathoracic impedance versus time for a patient with symptoms of congestive heart failure (CHF).

FIG. 3 shows a plot 300 of impedance versus time, specifically days before hospitalization of a patient. At 14 days prior to hospitalization, a relative impedance baseline is determined to be about 78 ohms; whereas, at time of hospitalization, impedance is about 60 ohms. As discussed further below, the impedance does not necessarily decrease in a linear manner from the baseline value to the CHF admission value. The data of the plot 300 suggest that a significant decrease in impedance occurred around −12 days followed by a substantially linear decrease from about −12 days to about −7 days. Thus, a decrease in impedance may result from varying mechanisms or phases (e.g., an onset phase followed by one or more subsequent phases).

Figure 4:
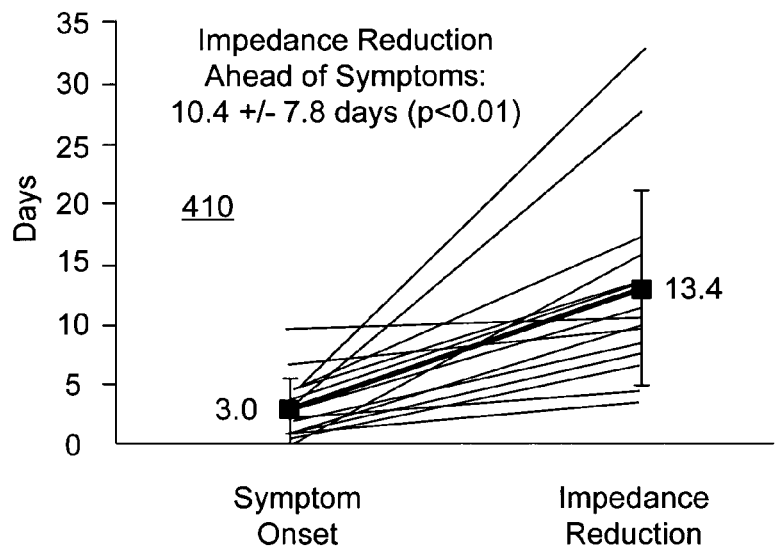
FIG. 4 is a series of plots of intrathoracic impedance information for various patients admitted for care due to CHF symptoms.
Figure 4:
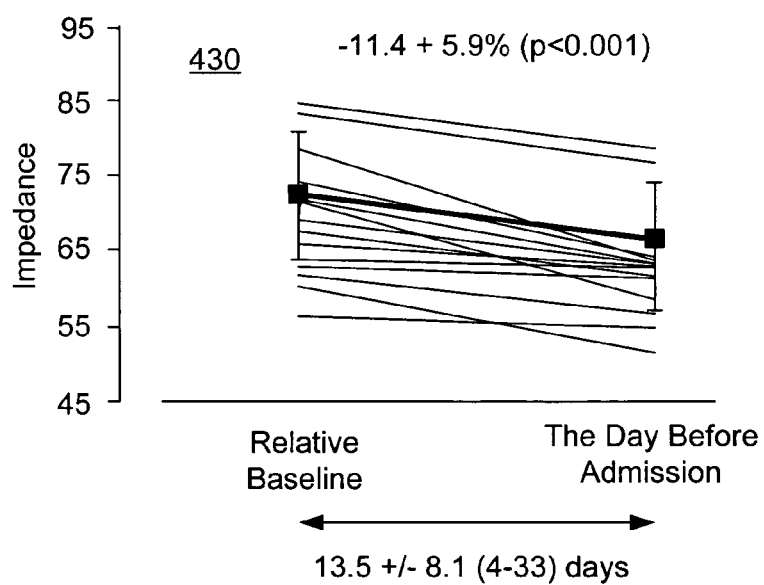

FIG. 4 shows a series of impedance-related plots 400, more specifically, two plots 410, 430 of impedance changes over time. The plot 410 includes impedance information from a series of patients. According to the plot 410, impedance reduction commenced an average of 10.4+/−7.8 days ahead of various symptoms (i.e., 13.4 days–3.0 days). The standard deviation yields a range for the series of patients from 18.2 days prior to symptoms to 2.6 days prior to symptoms. Thus, a patient dependence is suggested.

The plot 420 includes impedance information from a series of patients. According to the plot 420, the average impedance decreased from a relative baseline value to a lesser value on the day before admission related to various symptoms. The average relative baseline impedance of about 74 ohms decreased to about 66 ohms. In terms of percentage reduction, the impedance decreased by 11.4+/−5.9% for an average period of 13.5+/−8.1 days. The standard deviation yields a percentage reduction range for the series of patients from 17.3% to 5.5% for a range of days of 21.6 days to 5.4 days. Thus, as already mentioned with respect to the plot 410, a patient dependence is suggested.

Figure 5:
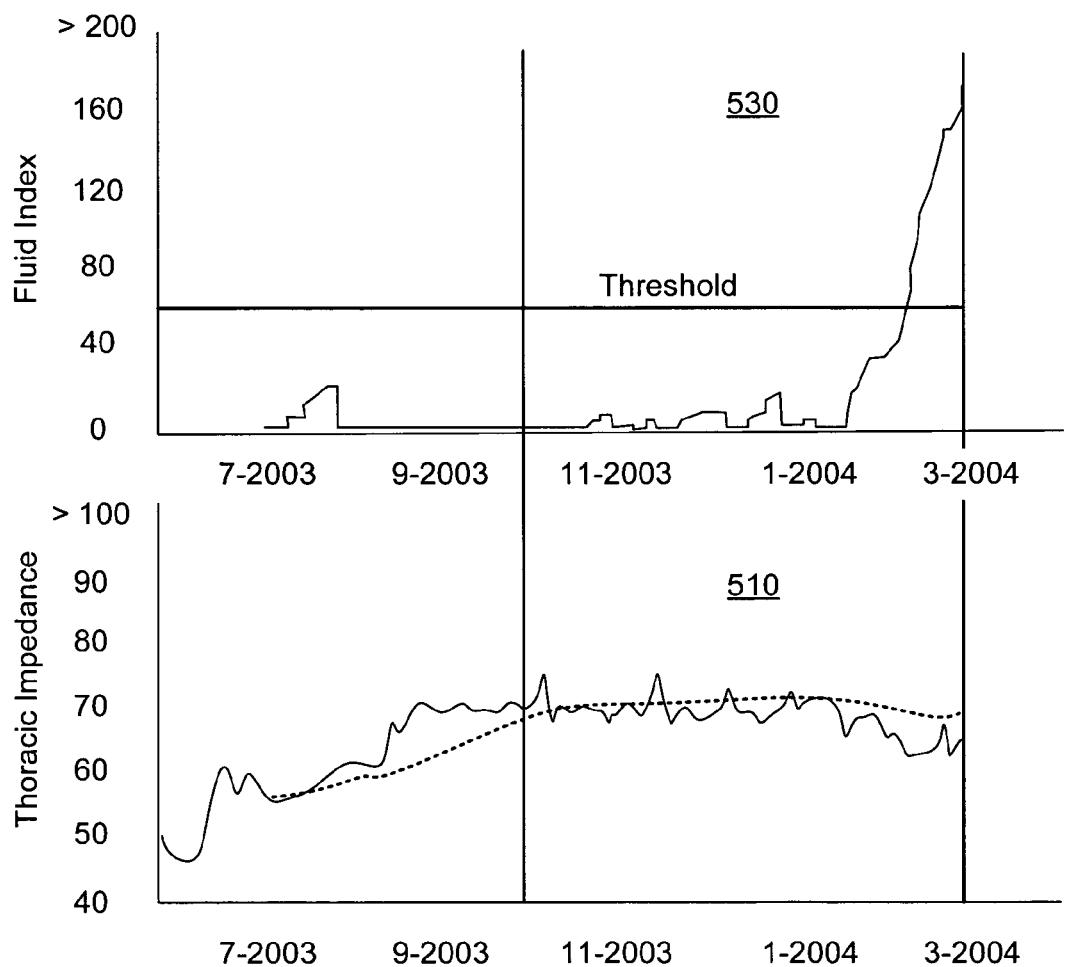
FIG. 5 is a series of plots that include a "fluid index" versus time based on thoracic impedance measurements.

FIG. 5 shows a scheme 500 that uses a "fluid index" that is based on thoracic impedance measured between a can or case electrode and a right ventricular defibrillation coil electrode. The scheme 500 is described in a report by Cowie, "Monitoring Heart Failure using an Implantable Device Measuring Intrathoracic Impedance—Technical and Clinical Overview", Business Briefing: *European Cardiology* 2005, pp. 62-65. The scheme 500 is illustrated using a plot 510 of thoracic impedance versus time and a plot 530 of fluid index versus time. According to the scheme 500, the plot 510 includes a daily impedance that is the average of each day's multiple impedance measurements and a reference impedance that adapts slowly to daily impedance changes. The plot 530 includes the fluid index, which is the accumulation of consecutive day-to-day differences between the daily and the reference impedance. In the scheme 500, a physician can activate the patient alert in the device and when a threshold is crossed the device will audibly alarm. Also, the fluid index is reset if the daily impedance readings become higher than the impedance trend to reduce the risk of an alarm when the lungs are drying out.

As described herein, various exemplary techniques account for patient dependence to allow for more accurate patient monitoring, for example, using impedance measurements. Also described herein, various exemplary techniques optionally rely on a multi-mechanism pulmonary edema model whereby impedance information may be analyzed for presence of, for example, an initial short-term phase (hours), a subsequent longer-term phase (days) or both short-term and long-term phases.

Figure 6:
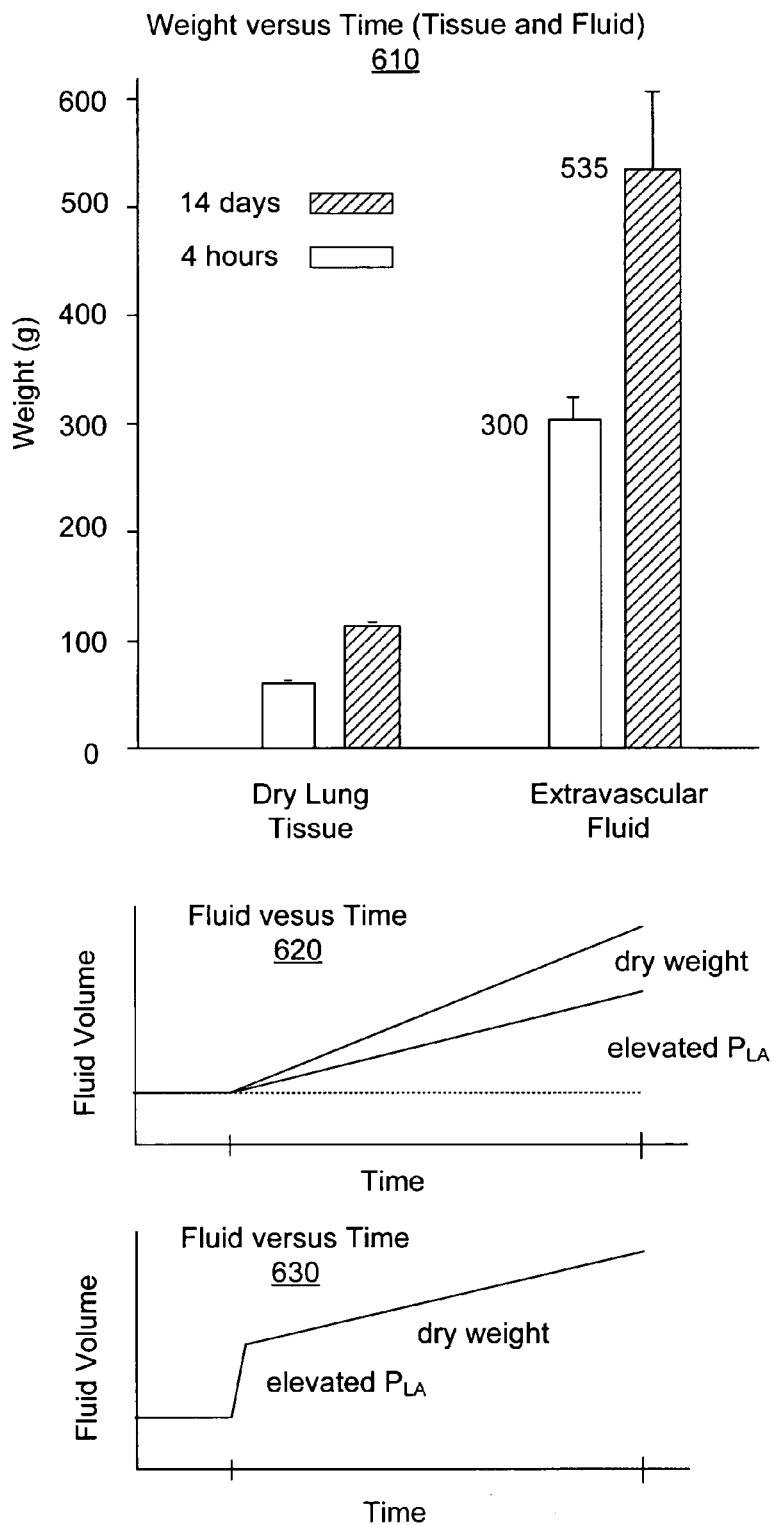
FIG. 6 is a series of plots that pertain to pulmonary edema.

With respect to a multi-mechanism model for pulmonary edema, FIG. 6 shows a plot 610 of dry lung tissue weight and extravascular fluid weight at four hours and at 14 days after elevation of left atrial pressure in sheep, as reported by Drake and Doursout, "Pulmonary edema and elevated left atrial pressure: four hours and beyond", *News Physiol Sci.* 2002 December; 17:223-6. FIG. 6 also shows plots 620, 630 which represent possible exemplary scenarios for edema.

Drake and Doursout prepared the plot 610 from data taken from a study by Erdmann et al., "Effect of increased vascular pressure on lung fluid balance in unanesthetized sheep", *Circ Res.* 1975 September; 37(3):271-84. Erdmann et al. observed that lymph flow reached a plateau within the first 4 hours of elevated left atrial pressure and, to test if lung fluid was steady after 4 hours, they maintained left atrial pressure at an elevated level for 14 days.

The report of Drake and Doursout pertains primarily to cardiogenic pulmonary edema, for example, caused by an increase in left atrial pressure when the left heart fails. An increase in left atrial pressure can cause rapid fluid accumulation within the lung interstitial spaces; however, the report suggests that, over the following days to weeks, additional fluid may accumulate due to the deposition of excess lung connective tissue. Thus, two phases exist wherein the latter phase is associated with more than one mechanism, for example, as hypothesized by Drake and Doursout, left atrial hypertension-related edema and fibrosis-related edema.

Referring again to the plot 610, the data indicate that significant fluid accumulation can occur over a course of days in response to elevated left atrial pressure. Further, the data of the plot 610 indicate that an increase in lung dry weight may accompany an increase in extravascular fluid. In general, if the left atrial pressure exceeds a critical level of about 25 mmHg, the volume of edema fluid will overwhelm the capacity of the interstitial spaces and fluid will flood the airways and alveoli. While such airway edema interferes with gas exchange and can result in death, many people live for months or years with modestly elevated left atrial pressure (e.g., left atrial pressure less than about 25 mmHg).

Thus, the report of Drake and Doursout suggests that sustained, subcritical left atrial pressure elevations lead to two phases of change in the lungs whereby the second phase may be associated, in part, with a mechanism that acts to increase lung dry weight. In particular, the first phase involves acute edema that develops in the first few hours of elevated left atrial pressure and the second phase involves a "persistent" edema associated with long-term (e.g., days or more) elevation of left atrial pressure that does generally not exceed a critical level.

As to underlying mechanisms, any heart disease that leads to increased left atrial pressure will cause typically some degree of pulmonary edema; however, an increase in lung connective tissue (pulmonary fibrosis) is common in patients with chronic heart disease. Such fibrosis may be a typical response to the persistence of edema fluid in almost any organ. Thus, Drake and Doursout suggest a persistent edema hypothesis whereby dry lung tissue weight should be increased due to the increase in connective tissue within the lung after a prolonged period of elevated left atrial pressure. According to this hypothesis, the extravascular fluid-to-dry tissue weight ratio might remain almost unchanged during a prolonged period of elevated left atrial pressure. In the plot 610, the data indicate that lung dry weight and extravascular fluid were each about 75% higher after 14 days versus 4 hours of elevated left atrial pressure and thus suggest that a large amount of edema fluid accumulated in the Erdmann et al. sheep long after the first 4 hours of elevated left atrial pressure. This evidence supports the persistent edema hypothesis.

Referring again to the plot 300 of FIG. 3, a substantial decrease in intrathoracic impedance occurs over a period of 14 days prior to admission. However, as already mentioned, a fairly large drop in impedance occurs around day −12. Thus, the intrathoracic impedance data of the plot 300 may also support the persistent edema hypothesis of Drake and Doursout or other hypothesis that accounts for fluid accumulation over a period of days.

The plots 620, 630 of FIG. 6 show possible scenarios whereby more than one mechanism is involved in edema. The plot 620 indicates that fluid volume increases in part due to elevated left atrial pressure and in part due to an increase in lung dry weight, which acts to increase fluid volume. The plot 630 indicates that a rather abrupt increase occurs in left atrial pressure such that lung fluid volume increases in a short period of time whereas a subsequent increase occurs due to an increase in lung dry weight, which acts to increase fluid volume. Of course, an elevated left atrial pressure may exist throughout the increase in lung fluid volume.

Figure 7:
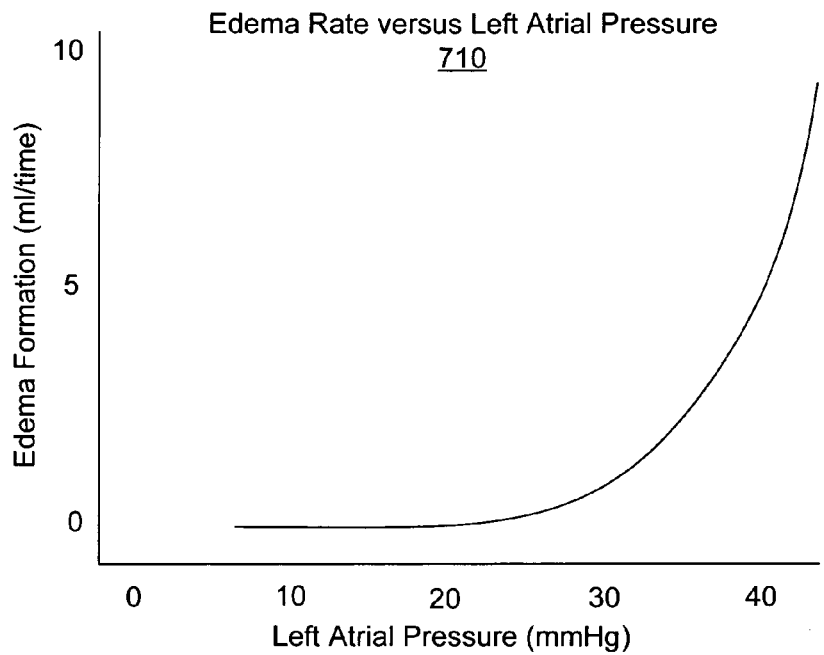
FIG. 7 is a plot and exemplary tables of information related to left atrial pressure where a weight may depend at least in part on left atrial pressure or NYHA class.

FIG. 7 shows an approximate plot 710 of edema formation (ml/time) versus left atrial pressure (mmHg). Lung capillary pressure in healthy humans at rest ranges between about 6 mmHg and about 10 mmHg and an increase in left atrial pressure causes a rise in lung capillary pressure, which directly affects transendothelial fluid dynamics. A sufficient rise in lung capillary pressure results in the formation of hydrostatic lung edema. Further, as left atrial pressure increases, a critical value is reached whereby edema formation reaches dangerous rates that can lead to death in a short period of time. Such critical values may be associated with capillary stress failure, which may also occur in response to long periods of "sub-critical" yet elevated left atrial pressure.

Various phases and associated mechanisms for edema have already been mentioned. With respect to fluid location within the lungs, an elevated left atrial pressure generally causes excess fluid to accumulate in the interstitial spaces of the lungs. Such interstitial fluid accumulation may occur with few or no associated clinical symptoms. In humans, the interstitium can only accommodate a few hundred milliliters of excess fluid so the fluid soon floods the airspaces, which in a 70 kg adult approximates 5,000 ml. Airspace flooding is associated with profound respiratory distress because the acini can no longer effectively exchange gases. Thus, a situation may become critical (i.e., life threatening) even where the elevated left atrial pressure does not reach critical values.

As indicated by the plot 710, the rate of fluid transfer to the lungs depends on left atrial pressure. Of course, the rate of fluid accumulation and amount of fluid accumulated depends on the rate of fluid removal as well. Further, external pressure can play a role, for example, consider high-altitude edema and positive airway pressure as a form of treatment. However, in all of these instances, left atrial pressure is a factor. In general, cardiogenic edema is associated with elevated left atrial pressure. Non-cardiogenic forms of edema may or may not be associated with left atrial pressure. Non-cardiogenic causes of edema may be related to a pharmaceutical, narcotic overdose, chemotherapy, salicylate intoxication, calcium antagonist overdose, hydrochlorothiazide, contrast fluids, high-altitude, neurogenic, pulmonary embolism, eclampsia, post cardioversion, post anaesthesia, post cardiopulmonary bypass, etc.

FIG. 7 also shows an exemplary table 720 and an exemplary table 730 that include exemplary weights that depend on left atrial pressure. The exemplary table 720 includes a percentage threshold (Y) column where the weight ($W_Y$) is used to adjust a threshold for use in impedance monitoring. The threshold (Y) may be determined on the basis of many patients. For example, data of the plots of FIG. 4 may be used to determine an average threshold. In general, the threshold (Y) represents a particular percentage decrease in intrathoracic impedance from a base value that warrants triggering an alarm or other action. The threshold (Y) may be for any suitable time period and may optionally be directed to a short-term phase or a long-term phase. For example, a short-term phase may pertain to lung filling without any significant increase in lung dry weight (e.g., due to fibrosis, etc.); whereas a long-term phase may pertain to lung filling associated with an increase in lung dry weight (e.g., due to fibrosis, etc.). Further, the threshold (Y) may be directed to an interstitial filling phase or a subsequent airspace filling phase. For example, the threshold (Y) may represent a percentage value that indicates a change from interstitial filling to airspace filling.

The exemplary table 730 includes an ohms-days threshold ($I_{OD}$) column where the weight ($W_I$) is used to adjust a threshold for use in impedance monitoring. The threshold ($I_{OD}$) may be determined on the basis of many patients. For example, data of the plots of FIG. 4 may be used to determine an average threshold. In general, the threshold ($I_{OD}$) represents a particular number of ohms-days or ohms-days differential based on intrathoracic impedance measurements that warrants triggering an alarm or other action. The threshold ($I_{OD}$) may be for any suitable time period and may optionally be directed to a short-term phase or a long-term phase. For example, a short-term phase may pertain to lung filling without any significant increase in lung dry weight (e.g., due to fibrosis, etc.); whereas a long-term phase may pertain to lung filling associated with an increase in lung dry weight (e.g., due to fibrosis, etc.). Further, the threshold ($I_{OD}$) may be directed to an interstitial filling phase or a subsequent airspace filling phase. For example, the threshold ($I_{OD}$) may represent a percentage value that indicates a change from interstitial filling to airspace filling.

CHF has been classified by the New York Heart Association (NYHA) into four classes of progressively worsening symptoms and exercise capacity. Class I corresponds to no limitation wherein ordinary physical activity does not cause undue fatigue, shortness of breath, or palpitation. Class II corresponds to slight limitation of physical activity wherein such patients are comfortable at rest, but wherein ordinary physical activity results in fatigue, shortness of breath, palpitations, or angina. Class III corresponds to a marked limitation of physical activity wherein, although patients are comfortable at rest, even less than ordinary activity will lead to symptoms. Class IV corresponds to inability to carry on any physical activity without discomfort, wherein symptoms of CHF are present even at rest and where increased discomfort is experienced with any physical activity.

The change was made in order to clarify what the NYHA classes are. NYHA classes are well-known to one of ordinary skill in the art (see, for example. Col. 1, lines 49-64 of U.S. Pat. No. 6,645,153; Col. 3, lines 11-29 of U.S. Pat. No. 6,045,513; paragraphs 8-11 of US 20020183584 A1) and the specification clearly sets forth using NYHA classes. Therefore, an inclusion of the definitions of the classes would not constitute new matter.

Also included in each of the tables 720, 730 is a NYHA class column. Thus, NYHA class or left atrial pressure may be used to determine a weight for a patient and, in turn, a threshold. The NYHA classes generally pertain to congestive heart failure, which is often due to left-sided dysfunction. For example, when the left ventricle is unable to pump out enough of the blood it receives from the lungs, pressure increases inside the left atrium and then in the pulmonary veins and capillaries, causing fluid to be pushed through the capillary walls into the air sacs. Heart valve problems may also contribute to congestive heart failure. For example, in mitral or aortic valve disease, the valves that regulate blood flow either do not open wide enough (e.g., stenosis) or do not close completely (e.g., aortic or mitral valve insufficiency), which allows blood to flow backward through the valve. When the valves are narrowed, blood cannot flow freely into the heart and pressure in the left ventricle builds up, causing the left ventricle to work harder and harder with each contraction. The increased pressure extends into the left atrium and then the pulmonary veins, causing fluid to accumulate in the lungs. If a mitral valve leaks, some blood may backwash toward the lung each time the heart pumps. If the leakage develops suddenly because of the snapping of the valve cord, a patient may develop sudden and severe pulmonary edema.

While the tables 720, 730 provide two examples, various other manners may exist to determine one or more thresholds as described herein. Further, an exemplary method may include more than one threshold. For example, a percentage threshold may be used for a filling phase while a ohms-days threshold may be used for a persistent edema phase associated with an increase in lung dry weight (e.g., due to fibrosis). While the threshold ($I_{OD}$) is termed "ohms-days", other impedance units or time units may be used.

While the tables 720, 730 include physiological parameters like LA pressure and NYHA class, other parameters may be used as alternatives or in addition to LA pressure and/or NYHA class. For example, ejection fraction, cardiac dimensions, cardiac output, evidence of mitral regurgitation, amount of body fluid, work test (e.g., 6 minute work test), quality of life, etc., may be used together with weights, thresholds, ohm-days measures, etc. With respect to cardiac dimensions, one or more left ventricular dimensions may be used (e.g., peak diastolic, peak systolic, etc.). Of course, LA or RV dimensions may provide relevant information. Further, change in a dimension with respect to time may be used. For example, contraction dynamics for a chamber (e.g., LV diameter or axial length over a cardiac cycle) may be used as an indicator of patient condition.

Figure 8:
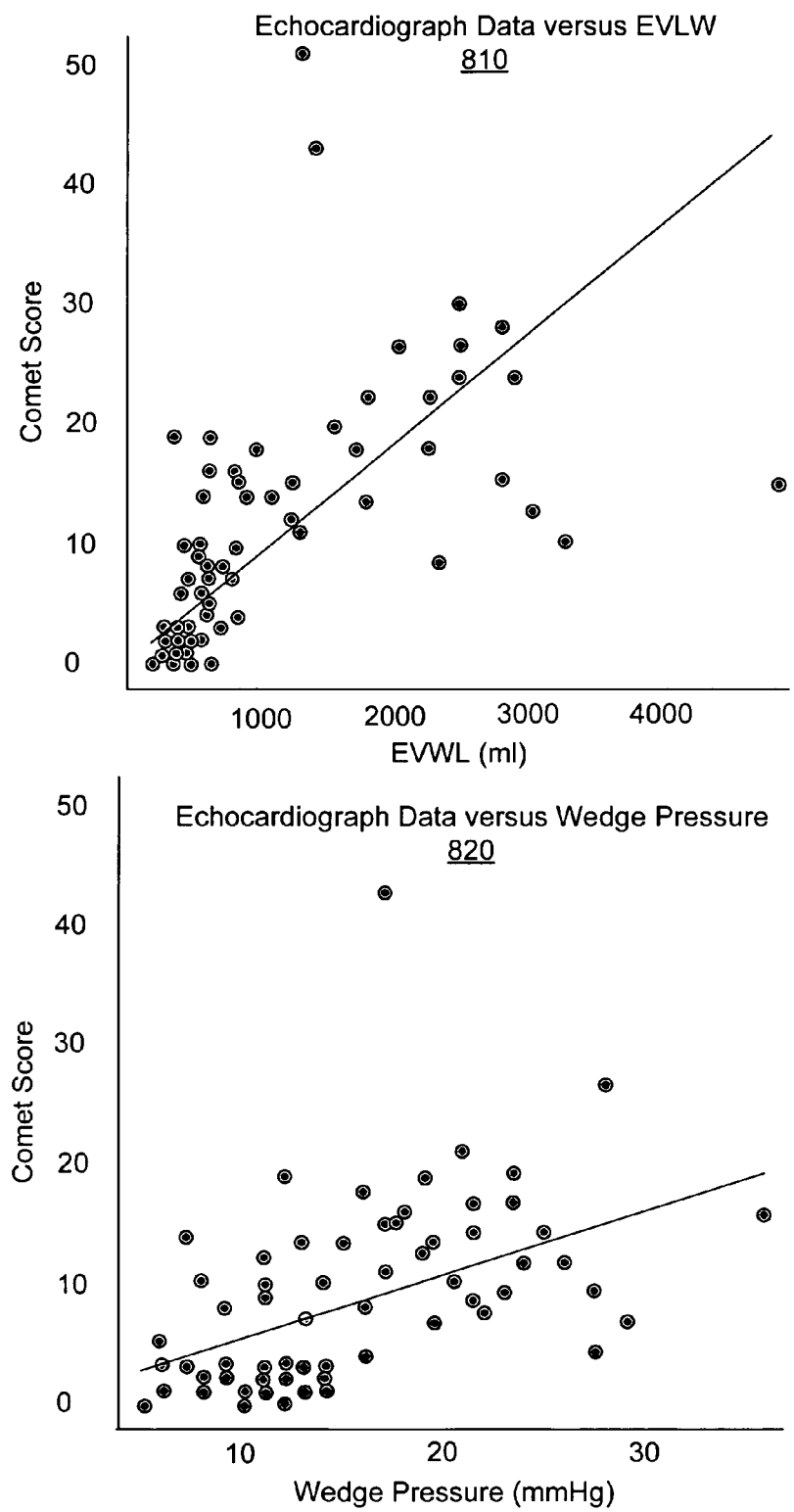
FIG. 8 is a series of plots pertaining to a comet score from echocardiograph information.

An exemplary method for determining a threshold for use in impedance monitoring optionally uses echocardiograph information. Echocardiograph information may pertain to cardiac function, pulmonary condition or both. Thus, in a single echocardiograph session, a care provider may determine cardiac function and pulmonary condition of a patient. FIG. 8 shows echocardiograph information from a study by Agricola et al., "Ultrasound Comet-tail Images: A Marker of Pulmonary Edema", *CHEST* 2005; 127-1690-1695, which is incorporated by reference herein. The Agricola study analyzed echocardiograph information for the presence and the number of "sonographic Kerley lines" to detect and quantify pulmonary edema.

The Agricola study performed echographic examinations of patients in the supine position. In the study, ultrasound scanning of the anterior and lateral chest was obtained on both the right and left hemithorax, the second to fourth (on the right side to the fifth) intercostals space, and the parasternal to midaxillary line. In each intercostals space, the number of comet-tail images was registered at the parasternal, midclavear, anterior, and middle axillary lines. The sum of the comet-tail images was provided as an echo comet score of the extravascular fluid of the lung. In the Agricola study, zero was defined as a complete absence of comet-tail images on the investigated area.

The Agricola study describes the comet-tail images as appearing when there is a marked difference in acoustic impedance between an object and its surroundings. In particular, the study notes that the reflection of the beam creates a phenomenon of resonance and the time lag between successive reverberations is interpreted as a distance, resulting in a center that behaves like a persistent source, generating a series of very closely spaced pseudo-interfaces. A normal lung contains much air and little water on the lung surface, so with ultrasounds no dense structures are visible in normal subjects.

Agricola et al. defined the comet-tail image as a hyperechogenic, coherent bundle with narrow basis spreading from the transducer to the further border of the screen. The comet-tail image described by Agricola extends to the edge of the screen (whereas short comet-tail artifacts may exist in other regions), and arises only from the pleural line. Agricola et al. noted that comet-tail images arising from the pleural line can be localized or disseminated to the whole lung surface, or again isolated or multiple, with a distance less than or equal to about 7 mm between two artifacts. Agricola et al. defined a positive (or pathologic) test result as bilateral multiple comet-tail images, either disseminated (defined as all over the anterolateral lung surface) or lateral (defined as limited to the lateral lung surface). Whereas, a negative test result was defined as an absence of comet-tail images, replaced by the horizontal artifact, or when rare, isolated comet-tail images were visible or when multiple comet-tail images were confined laterally to the last intercostal space above the diaphragm. The Agricola study used an ultrasound system (Sonos 5500; Phillips Medical Systems; Andover, Mass.) equipped with 1.8- to 3.6-MHz probe.

Agricola et al. scored echocardiograph information according to a scoring methodology. Using the methodology, thirty-two examination results were considered positive and 28 were negative. In a comparison of test results considered positive versus negative, a significant difference in mean extravascular lung water was found (742+/−277 mL vs 392+/−92 mL, p<0.0001). The mean content of EVLW in negative test result was below the assumed normal limit of EVLW (<500 mL).

The plot 810 presents comet score versus EVLW data where a positive linear correlation of R=0.42 (p<0.001) was found. The plot 820 presents comet score versus wedge pressure data where a positive linear correlation of R=0.48 (p<0.001) was found. Agricola et al. note that the number of comet-tail images can provide an indirect measurement of wedge pressure and that such an indicator is advantageous because the comet-tail images are detectable at a very early stage of pulmonary edema, appearing below the conventional detection threshold of alveolar edema. Again, alveolar or airspace edema is always preceded by interstitial edema, a constant feature of pulmonary edema.

An exemplary method uses echocardiograph information to determine a threshold for monitoring intrathoracic impedance. For example, such a method may include acquiring echocardiograph information, determining a degree or phase of edema and then determining a threshold for use in an implantable monitoring device. The threshold may alert a patient or care provider or cause other action. An exemplary method optionally uses more than one threshold. In such an exemplary method, at least one of the thresholds may optionally rely on echocardiograph information.

The presence of existing lung fluid may indicate that any subsequent change in impedance due to additional build-up of lung fluid will be relatively small whereas clearance of lung fluid may be an indicator of improved patient condition. An exemplary method optionally relates an increase in impedance to an improved patient condition for a patient with a deleterious preexisting level of lung fluid (e.g., a patient having pulmonary edema).

Figure 9:
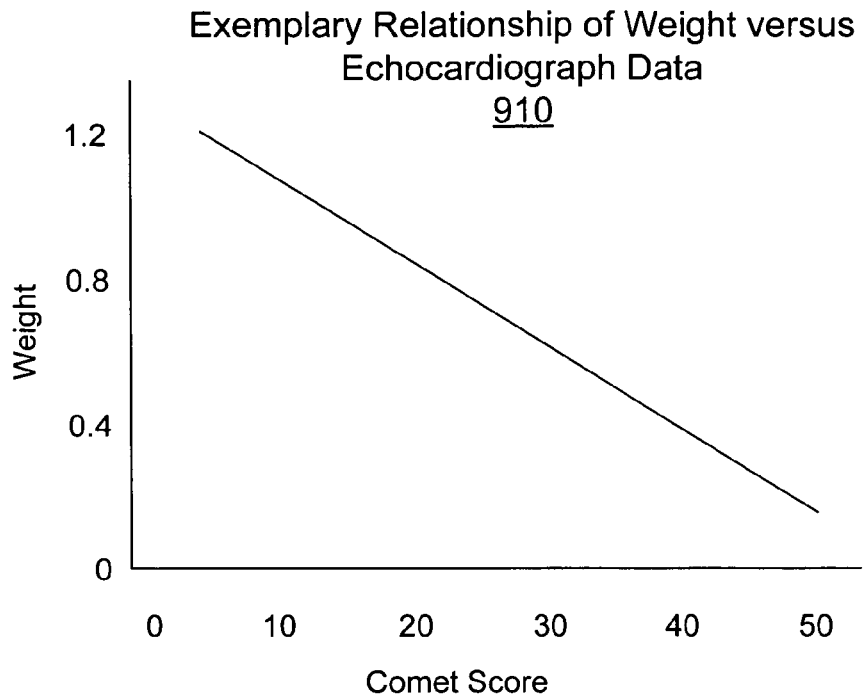
FIG. 9 is an exemplary plot of a weight as a function of comet score, various exemplary equations are also included.

FIG. 9 shows an exemplary plot 910 of comet score versus weight and various exemplary relationships, equations or models 930 where a weight is a function of comet score and optionally one or more other factors. The exemplary plot 930 indicates that as comet score increases, the weight decreases. As already mentioned, the weight may be used to adjust a standard threshold used in impedance monitoring. The relationship of the plot 910 acts to adjust a standard threshold based on comet score where a higher score indicates that a lower weight should be used and hence a lower threshold. For example, if a patient has symptoms of pulmonary edema, then the threshold should be diminished such that a small change in impedance acts to trigger an alarm or other action. In contrast, a patient that has a low comet score, the relationship of the plot 910 assigns a higher weight whereby a larger change in impedance must occur before an alarm or other action is triggered.

Any of the various exemplary equations 930 may be used to determine a weight based at least in part on comet score. For example, comet score alone may be used or comet score in conjunction with one or more other factors such as, but not limited to, NYHA class, left atrial pressure ($P_{LA}$), and wedge pressure ($P_{Wedge}$).

Figure 10:
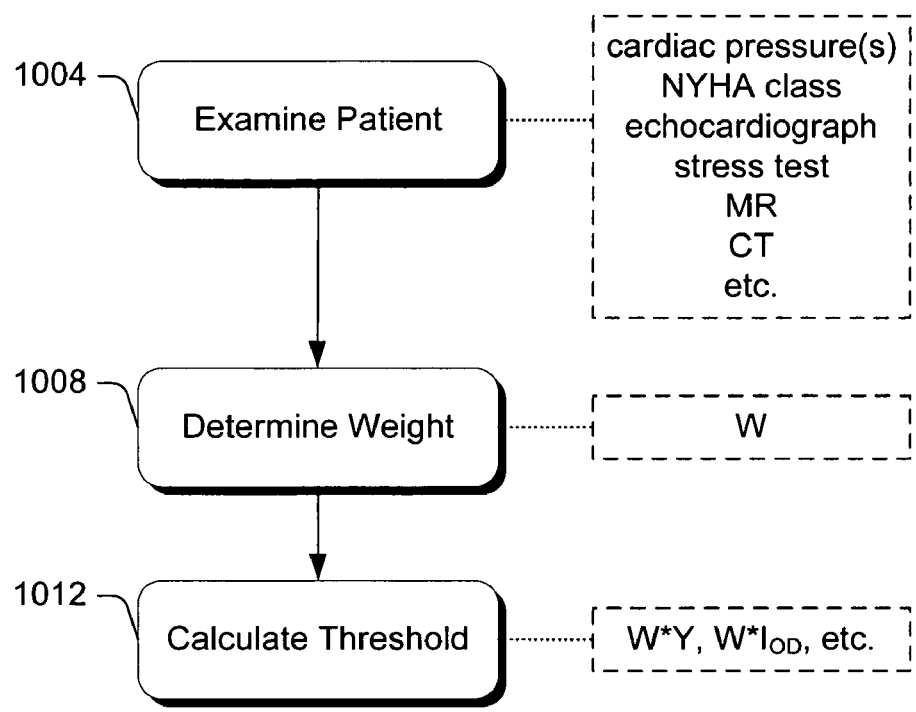
FIG. 10 is an exemplary method for calculating a threshold for use in monitoring intrathoracic impedance.

FIG. 10 shows an exemplary method 1000 for determining a weight and calculating a threshold based at least in part on the weight. An examination block 1004 includes examination of a patient or otherwise acquiring patient data (e.g., left atrial pressure, NYHA class, echocardiograph information, etc.). The examination or acquiring patient data may rely on invasive or non-invasive techniques. Further, such information may come from a device implanted in the patient.

Once at least some patient data is available, a determination block 1008 then relies on the patient data to determine a weight. In a calculation block 1012, calculation of a threshold occurs based at least in part on the weight. As already mentioned, the calculation may include multiplying a weight and a standard threshold to provide an adjusted threshold that accounts for patient condition or other patient related characteristics. In general, such a threshold is used in conjunction with impedance to determine patient condition. Impedance may be intrathoracic impedance, including intracardiac impedance.

An exemplary device (e.g., the device 100) includes a processor (e.g., the programmable controller 220), an impedance measuring circuit (e.g., the circuit 278) operably connected to the processor and control logic (e.g., various modules) operable in conjunction with the processor to acquire or determine a weight, to calculate a threshold based at least in part on the weight and to compare the threshold to one or more of an intrathoracic impedance, a change in intrathoracic impedance, and a product of intrathoracic impedance and time. In such an exemplary device, the control logic may optionally make other comparisons. In another example, the calculation of a threshold may occur outside the device and the threshold communicated to the device (e.g., using a device programmer). In various examples, the intrathoracic impedance is optionally an intracardiac impedance.

Figure 11:
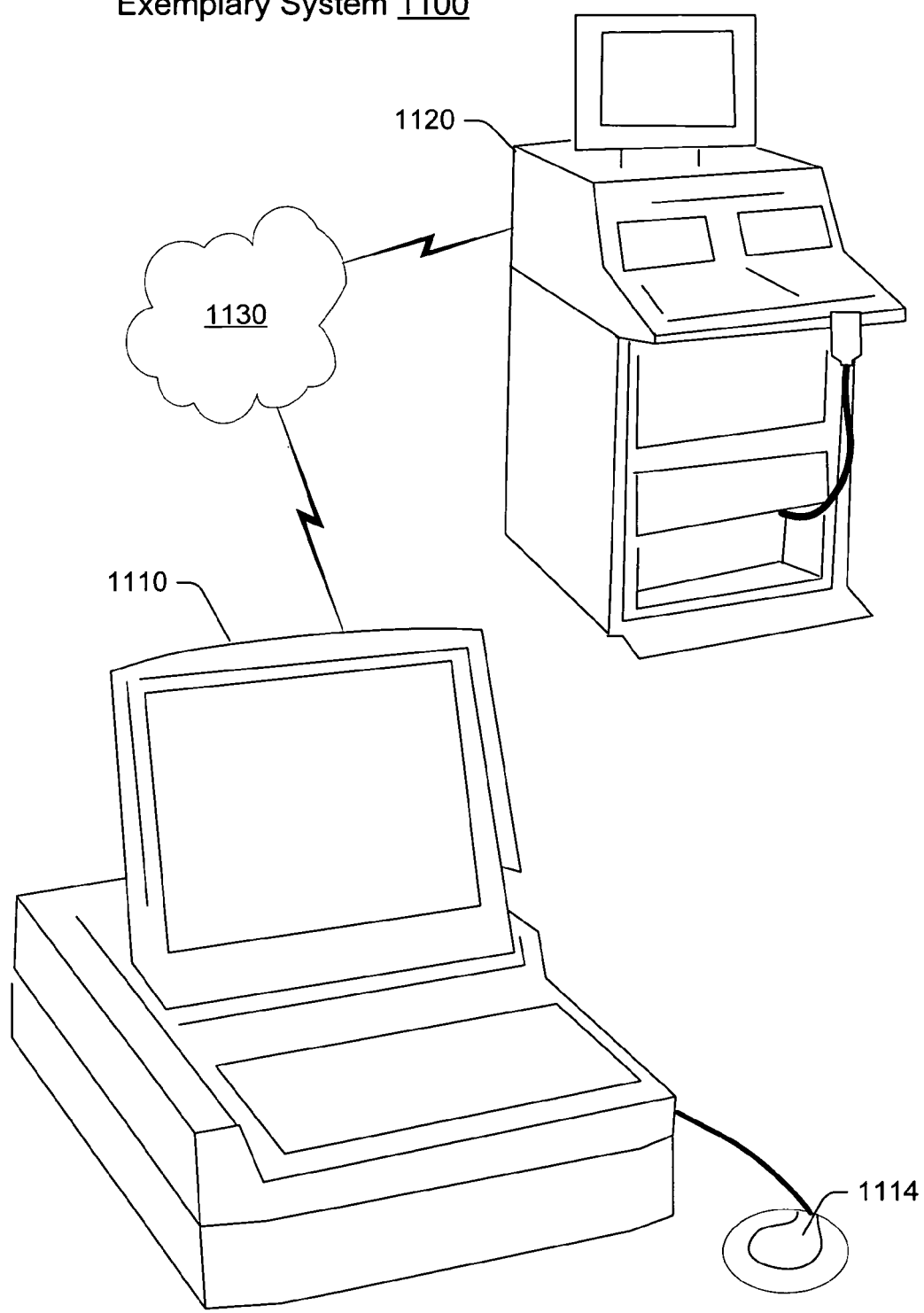
FIG. 11 is an exemplary system that includes a programmer for programming an implantable device for use in monitoring impedance.

FIG. 11 shows an exemplary system 1100 that includes a programmer 1110, an echocardiograph device 1120 and a communication path or network 1130. The programmer 1110 may have various features such as, but not limited to, various features of the St. Jude Medical 3510 programmer (St. Jude Medical, Inc., Sylmar, Calif.). The programmer 1110 includes a paddle or wand 1114 for communication with an implantable device (e.g., consider the device 100 of FIGS. 1 and 2). The programmer 1110 may rely on a communications network 1130 to access or to receive information from the echocardiograph device 1120. The echocardiograph device 1120 may be used to acquire echocardiograph information, which may be communicated to the programmer 1110 via the communication network 1130. The programmer 1110 may implement one or more exemplary methods or rely on various exemplary relationships to determine one or more criteria for use in monitoring impedance. Such criteria may be communicated to an implantable impedance monitoring device using the paddle 1114 or other device (e.g., telephone, etc.).

What is claimed is:

1. A method comprising:
   providing a New York Heart Association (NYHA) class of a patient;
   based on the NYHA class, determining a weight;
   based at least in part on the weight, determining a threshold for use in intrathoracic impedance monitoring of the patient;
   comparing an intrathoracic impedance of the patient to the threshold; and
   implementing control logic of a module, operable in conjunction with a processor, to decide, based on the comparing, whether to trigger a pulmonary edema alarm for the patient.

2. The method of claim 1 wherein the intrathoracic impedance comprises an intracardiac impedance.

3. The method of claim 1 wherein the threshold pertains to pulmonary edema occurring in a period of less than one day.

4. The method of claim 1 wherein the threshold comprises a percentage decrease in intrathoracic impedance from a base value or baseline.

* * * * *